United States Patent
Charles

(10) Patent No.: US 11,219,364 B2
(45) Date of Patent: Jan. 11, 2022

(54) AUTOMATIC XY CENTERING FOR DIGITAL MICROSCOPE

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 251 days.

(21) Appl. No.: 16/375,566

(22) Filed: Apr. 4, 2019

(65) Prior Publication Data

US 2019/0313902 A1    Oct. 17, 2019

Related U.S. Application Data

(60) Provisional application No. 62/656,079, filed on Apr. 11, 2018.

(51) Int. Cl.

| | |
|---|---|
| *A61B 3/13* | (2006.01) |
| *A61B 3/15* | (2006.01) |
| *A61B 3/00* | (2006.01) |
| *G02B 21/36* | (2006.01) |
| *A61B 3/14* | (2006.01) |

(52) U.S. Cl.
CPC .............. *A61B 3/13* (2013.01); *A61B 3/0025* (2013.01); *A61B 3/0058* (2013.01); *A61B 3/145* (2013.01); *G02B 21/367* (2013.01)

(58) Field of Classification Search
CPC ......... A61B 3/13; A61B 3/0025; A61B 3/145; A61B 3/0058; A61B 3/152; A61B 3/113; G02B 21/367
See application file for complete search history.

(56) References Cited

U.S. PATENT DOCUMENTS

| | | | |
|---|---|---|---|
| 6,175,642 B1* | 1/2001 | Gobbi | ................ G02B 21/0012 |
| | | | 348/172 |
| 2004/0133112 A1* | 7/2004 | Rajadhyaksha | ...... A61B 5/0059 |
| | | | 600/476 |
| 2006/0034543 A1 | 2/2006 | Bacus | |
| 2009/0021827 A1 | 1/2009 | Chong | |
| 2017/0092460 A1* | 3/2017 | Kiyohara | ................ H01J 37/20 |
| 2017/0292916 A1 | 10/2017 | Yang et al. | |
| 2017/0329123 A1 | 11/2017 | Sakamoto | |

FOREIGN PATENT DOCUMENTS

| | | |
|---|---|---|
| EP | 0740179 A1 | 10/1996 |
| JP | H05300521 A | 11/1993 |
| JP | 2008295804 A | 12/2008 |
| WO | WO2014040184 A1 | 3/2014 |

* cited by examiner

*Primary Examiner* — Mustak Choudhury

(57) ABSTRACT

A method and system are described for automatically centering in an XY plane a field of view of a patient's eye under high magnification during ophthalmic surgery. The method includes automatically moving the center of the field of view to the center of a circular image detected in a real-time video signal acquired from the field of view of the patient's eye under high magnification during ophthalmic surgery. The system configured to perform the method has a processor and a non-transitory computer-readable medium accessible to the processor containing instructions executable by the processor to perform the method.

14 Claims, 7 Drawing Sheets

AUTOMATIC XY CENTERING FOR DIGITAL MICROSCOPE

BACKGROUND

The present disclosure relates to ophthalmic surgery, and more specifically, to a method and system configured to allow automatic centering in an XY plane a field of view of a patient's eye under high magnification during ophthalmic surgery.

In ophthalmology, ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

During ophthalmic surgery, surgeons use a microscope to magnify visualization of a patient's eye or a part of the eye that is being operated on. During ophthalmic surgery, surgeons may use eyepieces, otherwise known as oculars, to view the eye or part thereof that is being magnified by the microscope. Alternatively, or in addition, during ophthalmic surgery, an image of the eye or part thereof that is magnified by the microscope may be displayed on a screen viewable by the surgeon and other personnel in an operating room. However, improvements in control of the display of the magnified image on the screen during ophthalmic surgery remains challenging.

SUMMARY

The present disclosure provides a system configured for automatically centering in an XY plane a field of view of a patient's eye under high magnification during ophthalmic surgery. The system includes a processor; and a non-transitory computer-readable medium accessible to the processor containing instructions executable by the processor for: acquiring, from a photosensor, a real-time video signal representing a field of view including the patient's eye under high magnification by a microscope, wherein the field of view includes an en-face XY plane; displaying on a display at least one view within the field of view corresponding to the real-time video signal; detecting a circular image in the real-time video signal, wherein the circular image includes a target image in the field of view; determining the location of the center of the circular image within the XY plane of the field of view; determining the location of the center of the field of view in the XY plane; comparing the location of the center of the circular image and the location of the center of the field of view; upon determining a difference in the locations of the center of the circular image and the center of the field of view, transmitting a movement instruction to a motorized microscope support configured to move the location of the microscope field of view in the XY plane, wherein the movement instruction directs movement of the microscope field of view to place the center of the field of view at the location of the center of the circular image; thereby automatically moving the center of the field of view to the center of the circular image detected in the real-time video signal acquired from the field of view of the patient's eye under high magnification during ophthalmic surgery.

The present disclosure also provides a method of automatically centering in an XY plane a field of view of a patient's eye under high magnification during ophthalmic surgery. The method includes the steps of: acquiring, by a processor executing instructions contained in a non-transitory computer-readable medium, from a photosensor, a real-time video signal representing a field of view including the patient's eye under high magnification by a microscope, wherein the field of view includes an en-face XY plane; displaying on a display, via the processor executing instructions contained in the non-transitory computer-readable medium, at least one view within the field of view corresponding to the real-time video signal; detecting a circular image in the real-time video signal, by the processor executing instructions contained in the non-transitory computer-readable medium, wherein the circular image includes a target image in the field of view; determining, by the processor executing instructions contained in the non-transitory computer-readable medium, the location of the center of the circular image within the XY plane of the field of view; determining, by the processor executing instructions contained in the non-transitory computer-readable medium, the location of the center of the field of view in the XY plane; comparing, by the processor executing instructions contained in the non-transitory computer-readable medium, the location of the center of the circular image and the location of the center of the field of view; and, upon determining a difference in the locations of the center of the circular image and the center of the field of view, transmitting, by the processor executing instructions contained in the non-transitory computer-readable memory, a movement instruction to a motorized microscope support configured to move the location of the microscope field of view in the XY plane, wherein the movement instruction directs movement of the microscope field of view to place the center of the field of view at the location of the center of the circular image; thereby automatically moving the center of the field of view to the center of the circular image detected in the real-time video signal acquired from the field of view of the patient's eye under high magnification during ophthalmic surgery.

In any of the disclosed implementations, the system and method may further include the following details:

i) the center of the field of view may correspond to a set location on the display;

ii) the set location on the display may be the center of the display;

iii) the display may be a rectangular display and the set location on the display may be a location at a mid-point between the long sides of the rectangular display;

iv) the circular image may correspond to an illuminated portion of the inside of the patient's eye viewable through a pupil of the eye;

v) the movement instructions transmitted to the motorized microscope head support may include a parameter of velocity, wherein the value of the velocity is variable as a function of distance between the location of the center of the field of view and the center of the circular image;

vi) the value of the velocity of the movement instructions may increase with increasing distance between the location of the center of the field of view and the center of the circular image;

vii) the value of the velocity of the movement instructions may increase linearly;

viii) the value of the velocity of the movement instructions may increase non-linearly;

ix) the magnification may have a zoom having a value; and the display may have an area; wherein the method further includes: detecting, by the processor, executing instructions contained in the non-transitory computer-readable medium, a diameter of the circular image; transmitting, by the processor, executing instructions contained in the non-transitory-computer-readable medium, an instruction to adjust the value of the zoom of the magnification so that the diameter of the detected circular image is fitted within a maximal portion of the area of the display; wherein the transmitting of the instruction to adjust the value of the zoom is selected from (a) transmitting an instruction to the microscope to adjust an optical zoom of the field of view of the microscope; and (b) transmitting an instruction to the display to adjust a digital zoom of the field of view of the real-time video signal;

x) the instructions contained in the non-transitory computer readable medium executed by the processor for the detecting of the circular image may include a circle Hough transform algorithm;

xi) the ophthalmic surgery may include a vitreoretinal surgery;

xii) the real-time video signal may be a 3D video signal; and xiii) the system may include an NGENUITY® 3D Visualization System.

BRIEF DESCRIPTION OF THE DRAWINGS

For a more complete understanding of the present disclosure, reference is now made to the following description, taken in conjunction with the accompanying drawings, in which:

FIG. 4 B shows another exemplary schematic of an XY plane overlaid on a circle detected in an image of an eye under magnification during ophthalmic surgery;

FIG. 4 C shows yet another exemplary schematic of an XY plane overlaid on a circle detected in an image of an eye under magnification during ophthalmic surgery;

DETAILED DESCRIPTION

Figure 1:
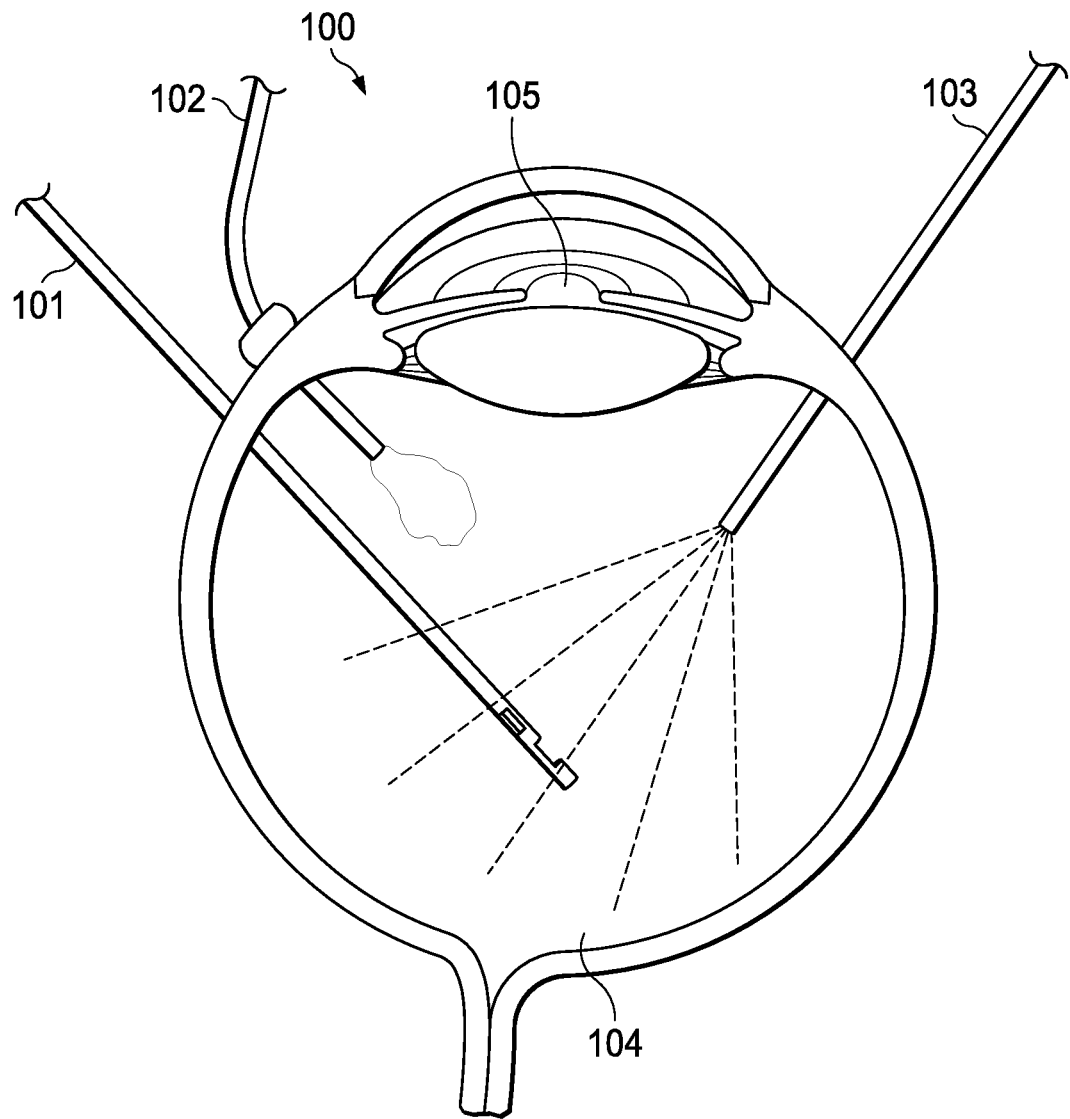
FIG. 1 shows an exemplary schematic showing a side view of an eye undergoing a vitreoretinal surgical procedure.

In the following description, details are set forth by way of example to facilitate discussion of the disclosed subject matter. It should be apparent to a person of ordinary skill in the art, however, that the disclosed implementations are exemplary and not exhaustive of all possible implementations.

The present disclosure relates to ophthalmic surgery, and more specifically, to a method to allow automatic centering in an XY plane a field of view of a patient's eye under high magnification during ophthalmic surgery, and a system configured to perform the method.

Ophthalmic surgery is performed on the eye and accessory visual structures. For example, vitreoretinal surgery encompasses various delicate procedures involving internal portions of the eye, such as the vitreous humor and the retina. The retina is a light-sensitive area that includes the macula, which is made up of light-sensitive cells that provide sharp, detailed vision. The vitreous humor of the eye is a clear gel that fills the space between the retina and the lens. The retina, the macula, and the vitreous body can all be subject to various diseases and conditions that can lead to blindness or vision loss and may require the attention of a vitreoretinal surgeon.

Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

Ophthalmic surgery often involves removal of eye tissue. For example, cataract surgery generally requires the removal and replacement of the lens. An artificial lens or intraocular lens implant can then be implanted within the eye to restore or improve the eyesight of the patient. Other procedures may also involve the removal of lens tissue and/or other types of eye tissue.

There are a number of procedures and devices that have been developed for the removal of eye tissue. For example, phacoemulsification is a widely used method for removal of diseased or damaged lens tissue. The phacoemulsification process generally involves insertion of a probe through a small corneal incision to break apart and remove the lens in cataract surgery.

In phacoemulsification, one or more incisions are generally made in the eye to allow the introduction of surgical instruments. The surgeon then removes the anterior face of the capsule that contains the lens inside the eye. An ultrasonic handpiece, where the tip vibrates at ultrasonic frequency, is generally used to sculpt and emulsify the cataract. After removal of the cataract, the posterior capsule is generally still intact and an intraocular lens implant (IOL) can be placed into the remaining lens capsule.

During ophthalmic surgery, because of the small size and delicate nature of the eye structures, surgeons typically use a microscope to magnify visualization of a patient's eye or a part of the eye that is being operated on. Typically, in the past, during ophthalmic surgery, surgeons used eyepieces, otherwise known as oculars, to view the eye or part thereof that is being magnified by the microscope. During ophthalmic surgery, stereo microscopes having two eyepieces viewable by both eyes simultaneously for binocular view are typically used. Some ophthalmic surgery procedures can take several hours to perform, and therefore previously, during ophthalmic surgery, ophthalmic surgeons would often be required to look through the binocular eyepieces of their microscopes for hours on end.

More recently, as an alternative to using eyepieces, or in addition, during ophthalmic surgery, developments in digital microscopy have allowed an image of the eye or part thereof that is magnified by the microscope to be displayed on a screen viewable by the surgeon and other personnel in an operating room. Among the benefits of using a display screen, rather than using microscope oculars, to visualize eye structures during ophthalmic surgery include decreased fatigue and increased comfort for the surgeon. In addition, unlike microscopes oculars, because the display can be viewed by more than one person at a time, the use of a display is useful for teaching and improves communication regarding the surgical procedure between personnel in the operating room.

Ophthalmic surgery visualization platforms utilizing digital microscopy and display screens applicable to the method and systems described herein generally include at least one high resolution photosensor such as a camera or charge coupled device (CCD) which is capable of receiving and acquiring a plurality of optical views of an eye under magnification by a microscope. Those skilled in the art will appreciate that receiving light in visible wavelengths in addition to wavelengths outside of the wavelengths of normal visible light is also within the scope of the present invention. In general, the high resolution photosensor then transmits a resultant real-time high-resolution video signal which is transmitted, via a processor executing instructions contained in a non-transitory computer readable medium, to at least one high resolution video display. In some configurations, because of the multiple high resolution optical views transmitted and presented on the display, the operator of the visualization platform, or others, is able to view a real-time high definition three-dimensional visual image of the target object or tissue.

Exemplary real-time visualization platforms suitable for implementing the system and practicing the methods described herein include those described U.S. Pat. Nos. 9,168,173, 8,339,447, and 8,358,330, all of which are incorporated herein by reference.

The term "display" as used herein refer to any device capable of displaying a still or video image. Preferably, the displays of the present disclosure display high definition (HD) still images and video images or videos which provide a surgeon with a greater level of detail than a standard definition (SD) signal. More preferably, the displays present such HD stills and images in three dimensions (3D). Exemplary displays include HD monitors, cathode ray tubes, projection screens, liquid crystal displays, organic light emitting diode displays, plasma display panels, light emitting diodes (LED) or organic LED (OLED), 3D equivalents thereof and the like. 3D HD holographic display systems are considered to be within the scope of the present disclosure.

The visualization platforms described herein include at least one high resolution photosensor. A photosensor is an electromagnetic sensor that responds to light and produces or converts it to an electrical signal which can be transmitted to a receiver for signal processing or other operations and ultimately read by an instrument or an observer. It may be capable of responding to or detecting any or all of the wavelengths of light that form the electromagnetic spectrum. Alternatively, the photosensor may be sensitive to a more restricted range of wavelengths including the at least one wavelength of light outside of the wavelengths of visible light.

An example of a photosensor which the visualization platforms described herein can include is a camera. A camera is a device used to capture images, either as still photographs or as sequences of moving images (movies or videos). A camera generally consists of an enclosed hollow with an opening (aperture) at one end for light to enter, and a recording or viewing surface for capturing the light at the other end. The recording surface can be chemical, as with film, or electronic. Cameras can have a lens positioned in front of the camera's opening to gather the incoming light and focus all or part of the image on the recording surface. The diameter of the aperture is often controlled by a diaphragm mechanism, but alternatively, where appropriate, cameras have a fixed-size aperture.

Exemplary electronic photosensors in accordance with the present disclosure include, but are not limited to, complementary metal-oxide-semiconductor (CMOS) sensors or charge-coupled device (CCD) sensors. Both types of sensors perform the function of capturing light and converting it into electrical signals. A CCD is an analog device. When light strikes the CCD it is held as a small electrical charge. The charges are converted to voltage one pixel at a time as they are read from the CCD. A CMOS chip is a type of active pixel sensor made using the CMOS semiconductor process. Electronic circuitry generally located next to each photosensor converts the received light energy into an electrical voltage and additional circuitry then converts the voltage to digital data which can be transmitted or recorded.

The real-time high-resolution video signal transmitted can be a digital video signal which is a digital representation of discrete-time signals. Often times, digital signals are derived from analog signals. As would be understood by persons skilled in the art, a discrete-time signal is a sampled version of an analog signal where the value of the datum is noted at fixed intervals (for example, every microsecond) rather than noted continuously. Where the individual time values of the discrete-time signal, instead of being measured precisely (which would require an infinite number of digits), are approximated to a certain precision—which, therefore, only requires a specific number of digits—then the resultant data stream is termed a "digital" signal. The process of approximating the precise value within a fixed number of digits, or bits, is called quantization. Thus, a digital signal is a quantized discrete-time signal, which in turn is a sampled analog signal. Digital signals can be represented as binary numbers, so their precision of quantization is measured in bits.

It will be appreciated by those of ordinary skill in the art that by attaching a photosensor to a visualization device such as a stereomicroscope which directs a plurality of views of a target object onto the photosensor the visualization systems described herein are able to acquire a plurality of optical views of a target object, such as a magnified eye during ophthalmic surgery, and transmit that information as a real-time high resolution video signal that can be recorded or presented for display and viewing. In some implementations, the transmitted digital video signal is capable of producing an image having a resolution of at least about 1280 lines by 720 lines. This resolution corresponds to the typically minimum resolution for what one of ordinary skill in the art would consider to be high definition or an HD signal.

"Real-time" as used herein generally refers to the updating of information at the same rate as data is received. More specifically, in the context of the present invention "real-time" means that the image data is acquired, processed, and transmitted from the photosensor at a high enough data rate and a low enough delay that when the data is displayed objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $1/30^{th}$ second of delay.

When the high resolution video signal is received and presented on a video display having corresponding high resolution or HD capabilities the resultant image provides a degree of clarity, detail, and control previously unattainable in the absence of high ambient visual light. Exemplary visual displays include cathode ray tubes, projection screens, liquid crystal displays, organic light emitting diode displays, plasma display panels and light emitting diode displays.

When the real-time high resolution video signal described herein includes multiple views of the target object or tissue the video display can be made three dimensional ("3D") so that depth of field is presented to the ophthalmic surgeon. Exemplary types of high resolution 3D video displays include stereoscopic 3D displays using polarized glasses such as those developed by TrueVision Systems, Inc. Alternatively, autostereoscopic 3D displays that do not require the use of any special glasses or other head gear to direct different images to each eye can be used. Similarly, holographic 3D displays are also contemplated as being within the scope of the present disclosure.

Examples of systems for digital microscopy that utilizes display screens for visualization during ophthalmic surgery include Alcon Laboratories NGENUITY® 3D Visualization System (Alcon, Inc. Corporation Switzerland, Hunenberg Switzerland), a platform for Digitally Assisted Vitreoretinal Surgery (DAVS). In particular, the NGENUITY® system is designed to enhance visualization of the back of the eye for improved surgeon experience. The NGENUITY® system refers to a system developed in collaboration with TrueVision® 3D Surgical (TrueVision Systems, Inc. Goleta Calif.). The NGENUITY® 3D Visualization System allows retinal surgeons to operate looking at a high definition 3D screen, instead of bending their necks to look through the eye-piece of a microscope. Traditional vitrectomy surgeries range from 30 minutes to over three hours in length to complete. This microscope eyepiece-free design is engineered to improve surgeons' posture and may reduce fatigue.

The NGENUITY® 3D Visualization System includes several elements, including a High Dynamic Range (HDR) camera that provides high resolution, image depth, clarity and color contrast. The HRD is a 3D stereoscopic, high-definition digital video camera configured to provide magnified stereoscopic images of objects during micro-surgery. The video camera functions as an addition to the surgical microscope during surgery and may be used to display real-time images or images from recordings. In particular, with the three-dimensional view, the surgeon has depth perception not previously available on standard television monitors. Surgeons may also increase magnification while maintaining a wide field of view as well as using digital filters to customize their view during each procedure, highlighting ocular structures and tissue layers which is imperative to visualize the back of the eye. Engineered with a specific focus on minimizing light exposure to the patient's eye, the NGENUITY® 3D Visualization System facilitates operating using lower light levels (Eckardt C and Paulo EB. Heads-up surgery for vitreoretinal procedures: An Experimental and Clinical Study. Retina. 2016 January; 36(1):137-47).

Despite the advantages described herein of displaying the magnified image on the screen during ophthalmic surgery, improvement in control of the display of the magnified image on the screen during ophthalmic surgery remains challenging.

For example, high magnification is needed to utilize the entire extent of the display, such as an NGENUITY® 55 inch OLED display at a distance, e.g., 4-6 feet, from the surgeon. During surgery, the position of the eye, or a portion of the eye that the surgeon intends to view, may move relative to the position of the microscope field of view in an XY plane corresponding to an en-face field of view. Movement may be due to movement of the patient during surgery, or movements associated with manipulation of the eye tissue during surgery. Accordingly, in order to maintain the portion of the eye that the surgeon intends to view in the field of view of the microscope, the position of the microscope in the XY plane must be reoriented so that the microscope's field of view is realigned with the position of the portion of the eye that the surgeon intends to view. In particular, the high magnification used during surgery means that even small movements during surgery may correspond to movement of the portion of the eye that the surgeon intends to view relative to the microscope's field of view, and as a result, movement of the real-time video image off the display screen. This can have the result that the surgeon is not able to effectively visualize the portion of the eye that the surgeon intends to view on the display screen.

Currently, centering of the magnified real-time video image on the screen is typically performed by manual control, such as manual operation of a foot switch joystick to drive XY motors in a box between a microscope support arm and the microscope head. In particular, very frequent surgeon control of the XY position on the microscope is required because of high magnification. In addition, manual control of the position of the magnified circular video image can be imprecise and problematic. For example, manual control may lead to sub-optimal centering of the image on the screen, or the real-time video image being positioned off-screen. In addition, manual control, such as using a foot switch joystick, can cause inadvertent motion of the surgeon's hand during surgery.

Given the need for fine-tuned control during ophthalmic surgery, improvements in equipment used by an ophthalmic surgeon to provide increased control over surgical techniques is expected to improve surgical outcomes for the patient.

The present disclosure generally relates to automatic centering of the magnified video image of the patient's eye on the screen viewed by the surgeon during ophthalmic surgery.

The term "high magnification" as used herein may refer to any value or range of magnification that may be typically used during ophthalmic surgery, such as vitreoretinal surgery, identifiable by skilled persons. For example, in some implementations, an exemplary high magnification may refer to a magnification value within a range of about 2× to 100×, or about 10× to 40×, or about 10× to 20×, among other ranges identifiable by skilled persons. In some implementations, high magnification may refer to a magnification value of about 20×.

Exemplary surgical microscopes that may be used with the system and method described herein include the Zeiss OPMI® Lumera T (Carl Zeiss Corporation, Germany), among other identifiable by persons skilled in the art. As would be understood by skilled persons, suitable microscopes may feature a magnification range, for example of approximately 3.5×-21.0× at a working distance of 200 mm, a motorized zoom system having a suitable zoom ratio such as 1:6 zoom ratio, a magnification factor γ, for example of approximately 0.4 to 2.4, and a focusing range of approximately 50 mm.

The total magnification of the system may be calculated by skilled persons by taking into account factors of the microscope and the photosensor, such as the focal length, the magnification factor set on the zoom components of the system, and the magnification factor of the photosensor, among other factors identifiable by skilled persons.

Methods and systems that include components having optical and/or digital zoom capability are contemplated in the present disclosure.

In general, it is understood that the term "automatic" refers to an action or a process that does not require manual control or manipulation by a user, such as an ophthalmic surgeon.

In particular, the term "automatic centering", as used herein in relation to a high magnification image of a patient's eye, refers to the control of centering of a magnified field of view that is performed by means of a computer processor executing instructions contained within a non-transitory computer-readable medium, as described herein.

In general, described herein is a method and system that utilizes video analysis software that detects a circle or an approximately circular image in a real-time video of a patient's eye during ophthalmic surgery and, in response, drives movement of the microscope's field of view XY position so the corresponding high magnification circular video image is centered on the display screen.

As would be understood by skilled persons, with regard to the detection of magnified images of eyes and structures within eyes during ophthalmic surgery, the term "circle" as used herein refers to an approximately circular shape and may include ellipses and approximately elliptical shapes.

In particular, the automatic XY image centering method and system described herein are useful for ophthalmic surgical procedures such as vitreoretinal surgery.

For example, FIG. 1 shows an exemplary schematic 100 showing a side view of an eye undergoing a vitreoretinal surgical procedure. Indicated in the schematic diagram are various tools inserted into the eye through incisions, including a vitrector cutting device 101 that removes the eye's vitreous gel in a slow, controlled fashion. Also shown is a cannula 102, used to replace fluid in the eye with a saline solution and to maintain proper eye pressure. Also shown is a light pipe 103, which provides illumination inside the eye. During a vitreoretinal surgery, such as shown in exemplary schematic diagram in FIG. 1, the ophthalmic surgeon visualizes the illuminated portion of the retina 104 using a microscope directed to view the internal part of the eye through the pupil 105.

Figure 2:
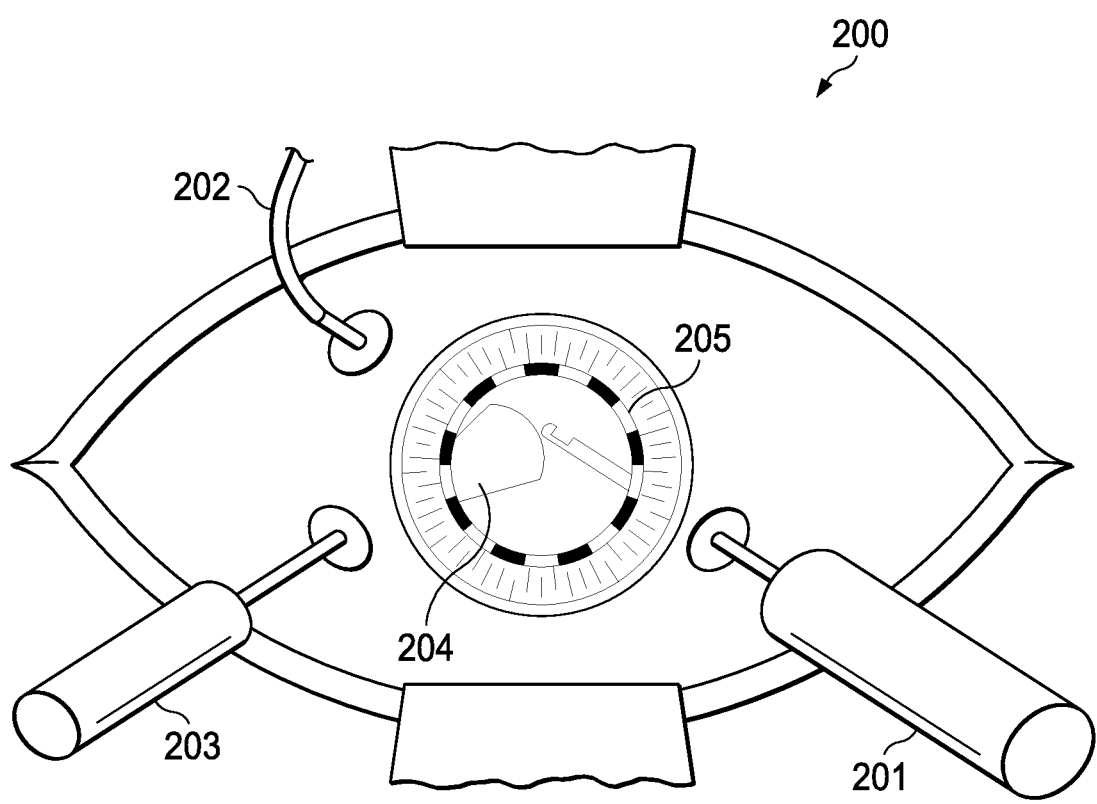
FIG. 2 shows a schematic showing an exemplary top-down view, corresponding to the en face view, of an eye undergoing an exemplary vitreoretinal surgical procedure.

FIG. 2 shows a schematic 200 showing an exemplary top-down view, corresponding to the en face view, of an eye undergoing an exemplary vitreoretinal surgical procedure, similar to the exemplary procedure shown in side-view in FIG. 1. Indicated in the schematic diagram are various tools inserted into the eye through incisions, including a vitrector cutting device 201, a cannula 202, and a light pipe 203, which provides illumination inside the eye. During a vitreoretinal surgery, such as shown in exemplary schematic diagram in FIG. 2, the ophthalmic surgeon visualizes the illuminated portion of the retina 204 using a microscope directed to view the internal part of the eye through the pupil, the outline of which is shown as a dashed circle 205.

During vitreoretinal surgery, for example, the field of view of the surgical microscope is often limited to a minute fraction of the whole retina. Typically, this minute fraction appears on the live real-time video image as a small patch of the retina on a predominantly dark background. The shape of the patch viewable by the ophthalmic surgeon via the microscope is determined by the shape of the pupil, which is usually a circular or elliptical disk. For example, the image may be elliptical when the retinal view is through an elliptical pupil of an eye rotated up, down, left, or right. Also, in some cases, the shape of the patch may include variations from a circular image according to variations in the shape of the iris of the eye, for example if the iris is absent, or part of the structure of the iris is absent or for example, if prior surgery has altered the shape of the iris.

The illuminated portion of the image of the eye may be referred to as the "target image" that the ophthalmic surgeon intends to view on a display during the surgical procedure. During surgery, the position of the illuminated patch may move relative to the position of the microscope field of view in an XY plane corresponding to the en-face field of view. Movement of the approximately circular illuminated patch may be due to movement of the patient during surgery, or movements associated with manipulation of the eye tissue during surgery. Accordingly, in order to maintain the image of the approximately circular illuminated patch in the field of view of the microscope, the position of the microscope in the XY plane must be reoriented so that the microscope's field of view is realigned with the position of the illuminated patch in the eye. In particular, the high magnification used during surgery means that even small movements during surgery may correspond to movement of the illuminated patch of the eye relative to the microscope's field of view, and as a result, movement of the real-time video image relative to the center of the display. This can have the result that the surgeon is not able to effectively visualize the illuminated patch of the eye on the display screen. As described herein, currently, this requires manual repositioning of the microscope's field of view, which has disadvantages as described herein. To solve this problem, the methods and systems described herein allow automatic centering of the image of the magnified eye on the display screen. As would be understood by skilled persons, the system and method of the present disclosure is suitable for ophthalmic surgery procedures that use endoillumination, wherein the term "endoillumination" as used herein refers to the illumination of the interior of the eye, as described herein and shown in the exemplary schematics in FIGS. 1 and 2. When using endoillumination, external microscopy illumination light sources, such as a microscope light source external to the eye, are turned off, so that the illuminated interior portion of the eye viewable as a circular or elliptical shape through the pupil of the endoilluminated eye is contrasted against a predominantly dark, non-illuminated exterior portion of the endoilluminated eye. For example, when using the exemplary NGENUITY® 3D Visualization System for performing vitreoretinal surgery, the interior of the eye is visualized by endoillumination, and external microscope light sources are turned off.

The term "XY plane" as used herein refers to the 2-dimensional space defined by an X axis and a Y axis, wherein the X axis is perpendicular to the Y-axis and the X axis and the Y axis intersect at a point referred to as the origin.

In particular, as used herein, the XY plane may refer to a plane that is typically approximately parallel to the ground, or the floor of the operating room, and in particular may form a plane that is approximately horizontal above the eye during ophthalmic surgery, while the patient is lying down, face up on an operating table. Thus, for example, the term X axis as used herein may refer to a horizontal axis that is oriented left-right relative to the position of the ophthalmic surgeon, and for example the term Y axis as used herein may refer to a horizontal axis that is oriented forward-backward (or distal-proximal) relative to the position of the ophthalmic surgeon. With respect to the field of view of the eye viewable through the microscope and the corresponding real-time video image that represents the field of view, the XY plane corresponds to the 2-dimensional space of the en-face view of the real-time video image. In some implementations, the real-time video signal is a 3D video signal, wherein in addition to the 2-dimensions of the en-face XY plane, the video signal also contains video data corresponding to the depth of the field of view in the Z axis, which is perpendicular to the XY plane.

It is understood that the XY plane may form a coordinate grid, wherein a coordinate refers to a position in the XY plane that is defined by the intersection of a value on the X axis and a value on the Y axis, wherein the values indicate a distance from the origin, wherein the origin may be nominally indicated by coordinates of X=0 and Y=0. Skilled persons will understand that XY coordinates generally relate to the Cartesian coordinate system, which is a system in which the location of a point is given by coordinates that represent its distances from perpendicular lines that intersect at a point called the origin. A Cartesian coordinate system in a plane has two perpendicular lines (the X-axis and Y-axis); in three-dimensional space, it has three (the X-axis, Y-axis, and Z-axis).

Figure 3:
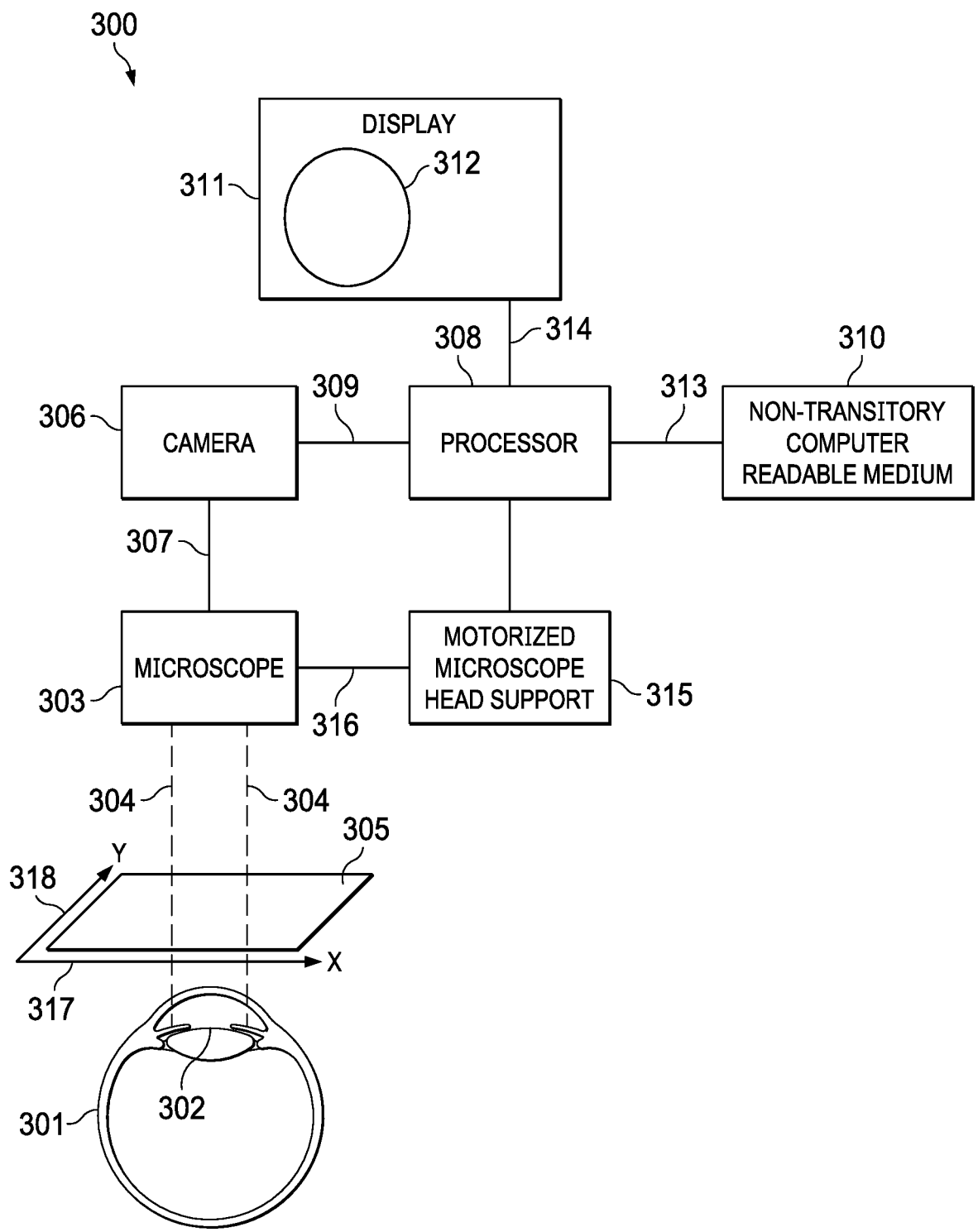
FIG. 3 shows a schematic of an exemplary system configured for automatic centering of the XY position of a circle detected in a magnified image of an eye by a digital microscope during ophthalmic surgery.

FIG. 3 shows a schematic of an exemplary system 300 configured for automatic centering of the XY position of a circle detected in a magnified image of an eye by a digital microscope during ophthalmic surgery. It is to be understood that the system 300 configured for automatic centering of the XY position of a circle detected in a magnified image of an eye by a digital microscope during ophthalmic surgery shown in FIG. 3 is exemplary and non-limiting, and that other configurations of the system 300 that are operative within the scope of the present disclosure are identifiable by persons skilled in the art. Modifications, additions, or omissions may be made to the system 300 without departing from the scope of the disclosure. The components and elements of the system 300, as described herein, may be integrated or separated according to particular applications. The system 300 may be implemented using more, fewer, or different components in some implementations.

FIG. 3 shows an eye 301 with pupil 302. A microscope 303 is shown, wherein an exemplary field of view 304 of the microscope 303 is shown as bounded by dashed lines. An XY plane 305 formed by an X axis and a Y axis, respectively indicated by arrows 317 and 318 is shown horizontally above the eye 301 and below the microscope 303. The microscope 303 is configured to be in electronic communication with a photosensor such as a camera 306 via an electronic connection 307 configured to allow the magnified image of the eye by the microscope 303 to be captured by the camera 306. In particular, the camera 306 is a video camera, such as a high definition video camera capable of capturing images at a high frame rate. The camera 306 is configured to be connected to and in electronic communication with a processor 308 via connection 309. The processor 308 is configured to execute instructions contained in a non-transitory computer readable medium 310 to receive digital real-time video image data from the camera 306 and transmit the real-time video image display data to a display 311. In FIG. 3, the display 311 is shown with a circular magnified image 312 detected in an image of a portion of an eye during ophthalmic surgery. For example, the circular image shown on the display may in some implementations be a circular or elliptical image of an illuminated portion of a retina visible to the microscope field of view through the pupil 302 of the eye 301 during vitreoretinal surgery. The processor 308 is in electronic communication with the non-transitory computer readable medium 310 via connection 313, and the processor 308 is in electronic communication with the display 311 via connection 314. The processor 308 is configured to execute instructions contained in the non-transitory computer-readable medium 310 to detect a circle in the digital image data received from the camera 306. A motorized microscope head support 315 is configured to move the microscope horizontally according to coordinates of the XY plane 305, in order to adjust the field of view of the microscope in the XY plane. Movement of the microscope via the motorized microscope head support 315 is controlled by the processor 308 executing instructions from the non-transitory computer readable medium 310. In particular, upon detection of a circular image in the digital real-time video image data of the magnified image of the eye, the processor 308, executing instructions contained in the non-transitory computer readable medium 310, is configured to send movement instructions to the motorized microscope head support 315 to position the center of the circular image in the center of the field of view 304 of the microscope 303. Accordingly, the processor 308, executing instructions contained in the non-transitory computer readable medium 310, transmits movement instructions to the motorized microscope head support 315 according to the XY plane to result in positioning the center of the circular image in the center of the display 311. Movement of the microscope 303 by the motorized microscope head support 315 is via connection 316.

The exemplary system shown in FIG. 3 may additionally include a control panel (not shown) having user operated controls that allow a surgeon to adjust the characteristics of the image data such as the magnification zoom, color, luminosity, contrast, brightness, or the like sent to the display 311.

Figure 4A:
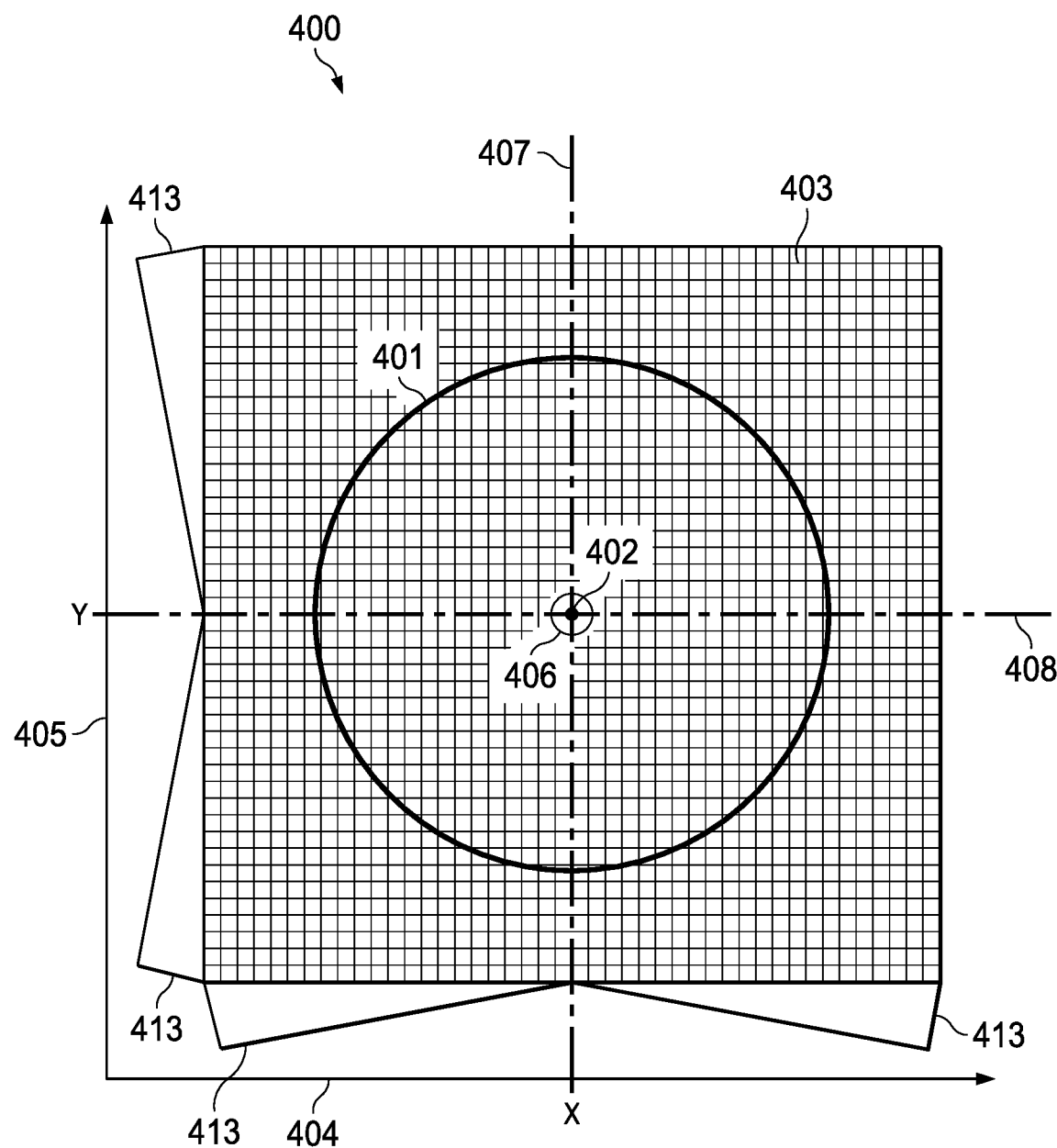
FIG. 4 A shows an exemplary schematic of an XY plane overlaid on a circle detected in an image of an eye under magnification during ophthalmic surgery.
Figure 4B:
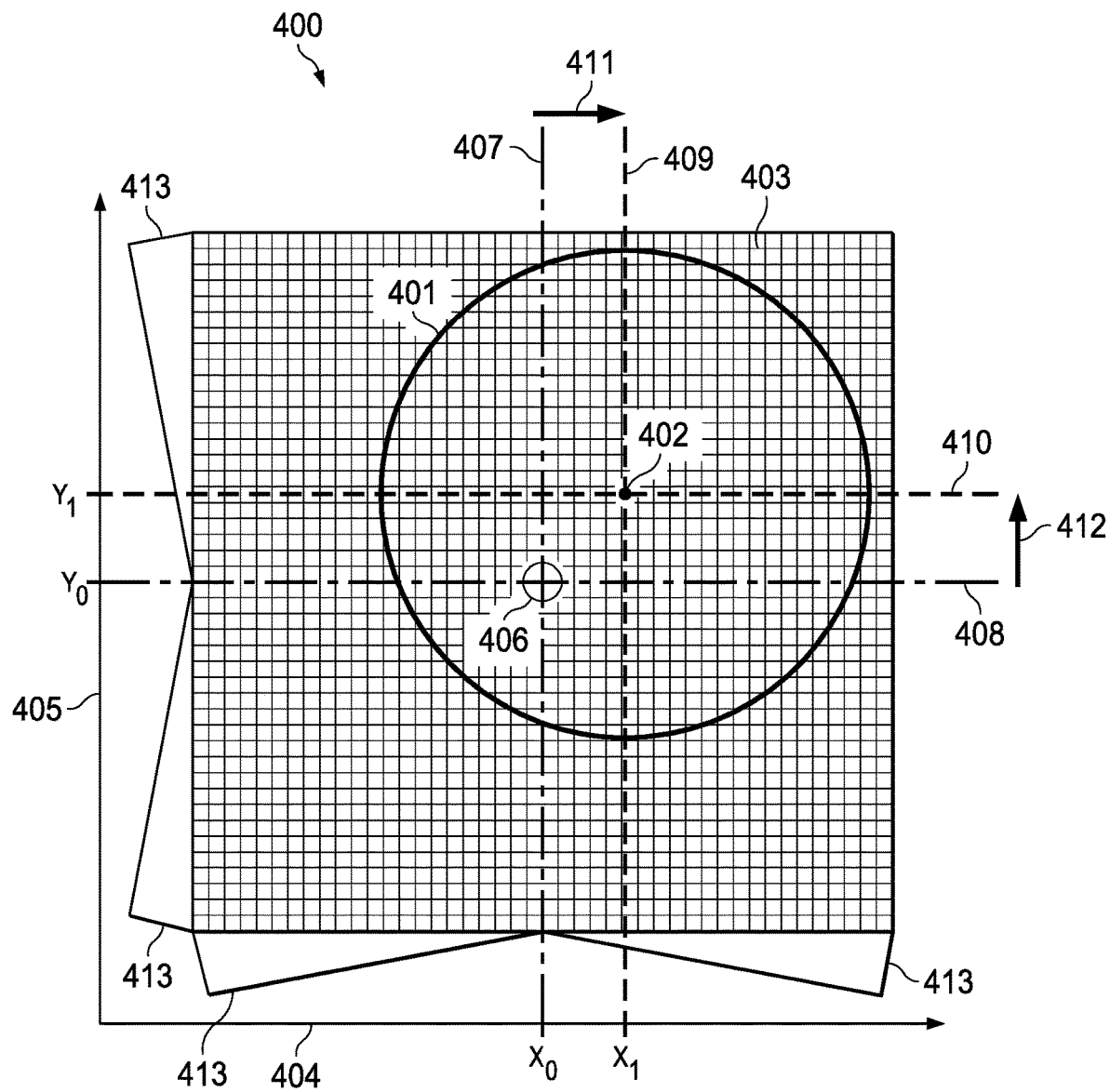

FIG. 4 A shows an exemplary schematic 400 of an XY plane 403 overlaid on a circle 401 detected in an image of an eye under magnification during ophthalmic surgery. For example, the circle 401 detected may be an illuminated internal portion of the eye viewable through the circular shape of the pupil, as depicted by the dashed circle 205 in FIG. 2. The circle 401 has a circle center 402 depicted as a solid black spot. The XY plane 403 indicates the area of the field of view of the microscope, and in particular the area of the field of view of the magnified image captured by the camera. The XY plane 403 formed by X axis 404 and Y axis 405 has a grid of XY coordinates. The XY plane is depicted as a grid of intersecting lines at points along the axes, however it is to be understood that the XY plane 403 forms a continuous horizontal plane field, so that the XY coordinates can have any X and Y values along the X and Y axes. The field of view may have any shape, such as a circle or a square. In an exemplary implementation, the field of view produced by the microscope and NGENUITY® optical system field stops is circular. In the exemplary schematic shown in FIG. 4 A, the XY plane 403 indicates a horizontal plane overlaid onto a field of view of a microscope used to visualize an eye under magnification during ophthalmic surgery. In FIG. 4 A, the field of view has a field of view center 406 indicated by a small circle. The center of the field of view center 406 is located at the XY coordinates intersected by lines 407 and 408, which have coordinate values of $X_0$ and $Y_0$, respectively. In some implementations, the field of view center 406 can be a single point located at the center of the field of view, whereas in other implementations, the field of view center 406 can be a region having an area, such as a circular area, or any other suitable shape that defines a center region of the field of view. In some implementations, the field of view center 406 may be a region having a set size relative to the total field of view, such as 1%, 5%, 10% or 20% of the total field of view. The circle center has XY coordinates having coordinate values of $X_1$ and $Y_1$, respectively. In FIG. 4 A, the circle center 402 is shown located in the same position as the center of the field of view center 406. When the circle center 402 is located in the same position as the field of view center 406, there is no difference between the coordinates of the circle center 402 and the field of view center 406, thus the absolute value of $X_1-X_0=0$ and the absolute value of $Y_1-Y_0=0$.

In contrast with FIG. 4 A, in FIG. 4 B the circle center 402 is shown located in a different position to the center of the field of view center 406. In FIG. 4 B, the field of view center 406 is shown located at coordinates $X_0$, $Y_0$, indicated by the intersection point of lines 407 and 408, respectively. In FIG. 4 B, the circle center 402 is shown located at coordinates $X_1$, $Y_1$, indicated by the intersection point of dashed lines 409 and 410, respectively. When the circle center 402 is located in a different position as the field of view center 406, there is a difference between the coordinates of the circle center 402 and the field of view center 406, thus the absolute value of $X_1-X_0>0$ and/or the absolute value of $Y_1-Y_0>0$.

The processor 308 is configured to execute instructions contained in the non-transitory computer-readable medium 310 to detect the circle center 402 and the field of view center 406. The processor 308 is also configured to execute instructions contained in the non-transitory computer-readable medium 310 to calculate the respective XY coordinates of the circle center 402 and the field of view center 406, and to detect a difference in the coordinates of the circle center 402 and the field of view center 406. Accordingly, upon detecting a difference between the coordinates of the circle center 402 and the field of view center 406, when the absolute value of $X_1-X_0>0$ and/or the absolute value of $Y_1-Y_0>0$, the processor, executing instructions contained in the non-transitory computer-readable medium, sends movement instructions to the motorized microscope head support 315 according to the XY plane to reposition the field of view center 406 at the same location as the circle center 402, to result in the absolute value of $X_1-X_0=0$ and the absolute value of $Y_1-Y_0=0$. For example, as shown in FIG. 4 B, upon detecting the position of the circle center 402 having coordinates different from the field of view center 406, the processor, executing instructions contained in the non-transitory computer-readable medium, sends movement instructions to the motorized microscope head support 315 to relocate the field of view center 406 as depicted as arrows 411 and 412.

The coordinates of the field of view center 406 and the circle center 402 may be values calculated relative to the origin, wherein the origin is the point of intersection of the X axis and the Y axis of the XY plane. The values may be any suitable units of distance such as mm or µm. The processor is configured to execute instructions contained in the non-transitory computer-readable medium to calculate the values of the coordinates in the XY plane, such as values relative to the origin. Accordingly, the values of X and Y coordinates increase with increasing distance from the origin. Thus, the positions of the field of view center 406 and the circle center 402 can be calculated, and the relative positions of the field of view center 406 and the circle center 402 in the XY plane can be calculated relative to the origin. Accordingly, for example, as shown in FIG. 4 A and FIG. 4 B, when the origin is placed proximally on the left side, the value of X increases from left to right, and the value of Y increases from proximal (back) to distal (forward). Thus, in the exemplary schematic shown in FIG. 4 B, the location of the circle center 402 is detected as being to the right and forward (more distal) than the field of view center 406, thus $X_1-X_0>0$ and $Y_1-Y_0>0$. In contrast, if the circle center 402 is located to the left and more proximal (back) than the field of view center 406, then the coordinates calculated relative to the origin would give $X_1-X_0<0$ and $Y_1-Y_0<0$. In both cases, when the circle center 402 is in a different location to the field of view center 406, the absolute value of $X_1-X_0>0$ and the absolute value of $Y_1-Y_0>0$.

Alternatively, for example, the coordinates of the XY plane may be calculated relative to the field of view center 406, so that the XY plane 403 of the field of view is divided into four quadrants divided by lines 407 and 408. Thus, as shown in FIG. 4 A and FIG. 4 B, the top left quadrant will have positive values of Y and negative values of X relative to the field of view center 406, the top right quadrant will have positive values of Y and positive values of X relative to the field of view center 406, the bottom left quadrant will have negative values of Y and negative values of X relative to the field of view center 406, and the bottom right quadrant will have negative values of Y and positive values of X relative to the field of view center 406. Thus, coordinates of a circle center 402 located in a position in any quadrant can be calculated relative to the field of view center 406.

In implementations described herein, the field of view center 406 may correspond to the center of the display 311. Accordingly, upon positioning the field of view center 406 at the same location as the circle center 402, the circle center is positioned at the center of the display 311.

The movement instructions sent to the motorized microscope head support 315 may have a parameter of velocity, for example measured in any suitable units such as mm/second or µm/second. For example, the velocity of the movement may be about 1 mm/second. Other velocity values may be used, such as from about 1 µm/second to 1 cm/second. In some implementations, the value of the velocity may be fixed, whereas in other implementations the value of the velocity may be variable. In some implementations, the value of the velocity may vary according to the relative positions of the circle center 402 and the field of view center 406. For example, as the absolute value of $X_1-X_0$ and/or the absolute value of $Y_1-Y_0$ increases, the velocity may increase. Accordingly, as the absolute value of $X_1-X_0$ and/or the absolute value of $Y_1-Y_0$ decreases, the velocity may decrease. As depicted in FIG. 4 A and FIG. 4 B, triangles 413 indicate a relationship of increasing velocity of the movement with increasing distance of the circle center 402 from the field of view center 406. In some implementations, the increase in velocity of movement with increase in distance of the circle center 402 from the field of view center 406 may be linear (for example, as depicted by triangles in FIG. 4 A and FIG. 4 B). In other implementations, the increase in velocity of movement with increase in distance of the circle center 402 from the field of view center 406 may be non-linear. For example, the increase in velocity may follow a curved function wherein the velocity increases by a multiplication factor proportional to the increasing distance between the circle center 402 and the field of view center 406.

In a preferred implementation, the movement velocity increases with increasing distance between the circle center 402 and the field of view center 406 and decreases with decreasing distance between the circle center 402 and the field of view center 406. Accordingly, preferably the method may be implemented, and the system so configured, to result in a slow ramping up and ramping down of the movement velocity with respective increasing or decreasing distance between the circle center 402 and the field of view center 406.

Accordingly, an object of the present invention is automatic computer processor-mediated centering in the microscope field of view and the linked display of the detected circle in the image of the magnified eye wherein the centering has smooth movement. In particular, an object of the invention is an automatically controlled response to detecting an 'off-center' circle image in a magnified eye that smoothly repositions the circle in the center of the field of view. The centering occurs in real-time upon capture and image processing of the live video of the magnified eye during ophthalmic surgery. In some implementations, the system is configured so that the velocity of the centering movement may be set according to user preference.

In some implementations, the absolute value of $X_1-X_0$ and/or the absolute value of $Y_1-Y_0$ may have a set minimum value before the processor 308 sends the movement instruction to the motorized microscope head support 315. Accordingly, the system described herein may allow some movement of the circle center 402 relative to the field of view center 406 before a repositioning of the microscope field of view is executed. For example, the position of the field of view center 406 may vary from the detected circle center 402 by a set distance or a set proportion of the field of view or the detected circle before the processor 308 sends the movement instruction to the motorized microscope head support 315. For example, in some implementations, the position of the field of view center 406 may vary from the detected circle center 402 by approximately 10% of the diameter of the of the field of view or the detected circle before the processor 308 sends the movement instruction to the motorized microscope head support 315.

Figure 4C:
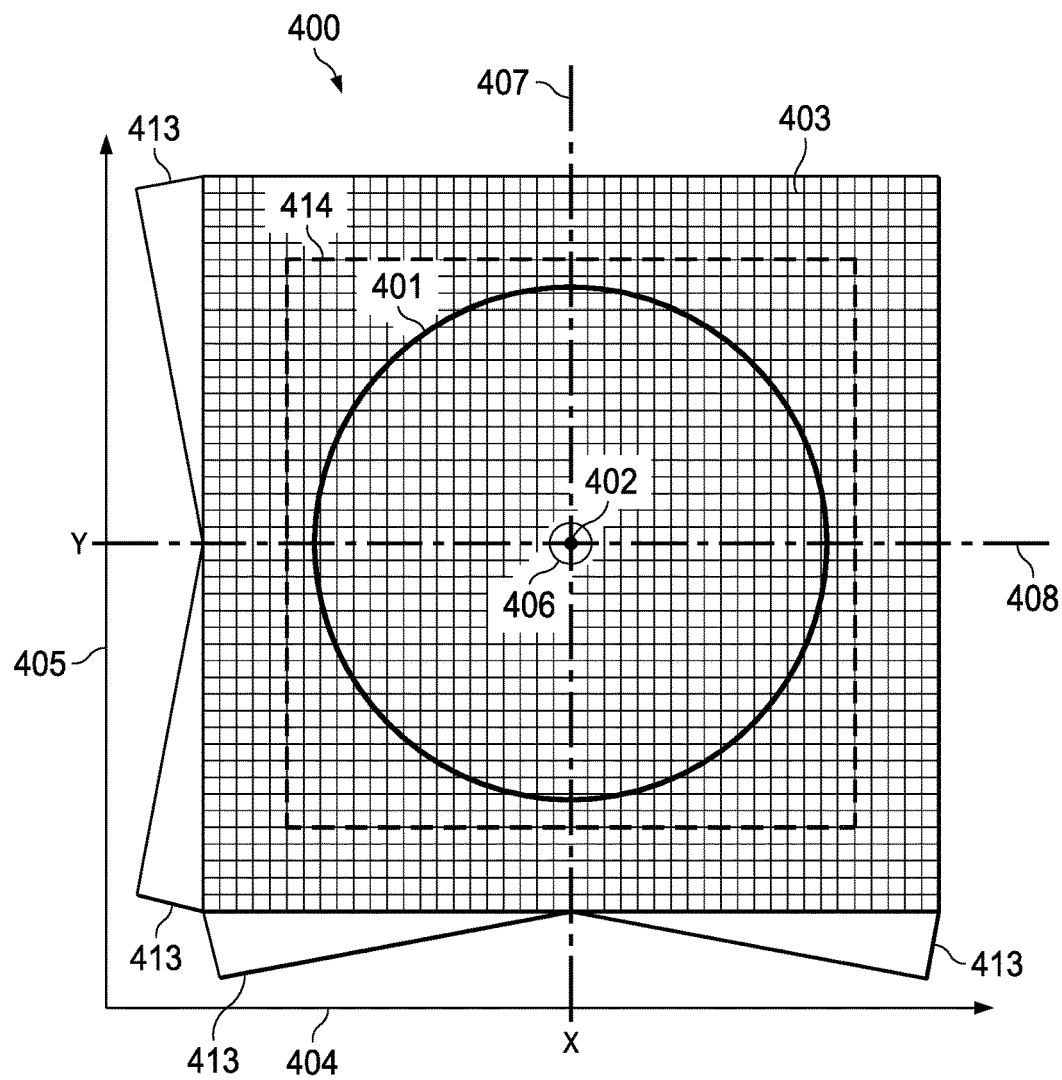
Figure 5:
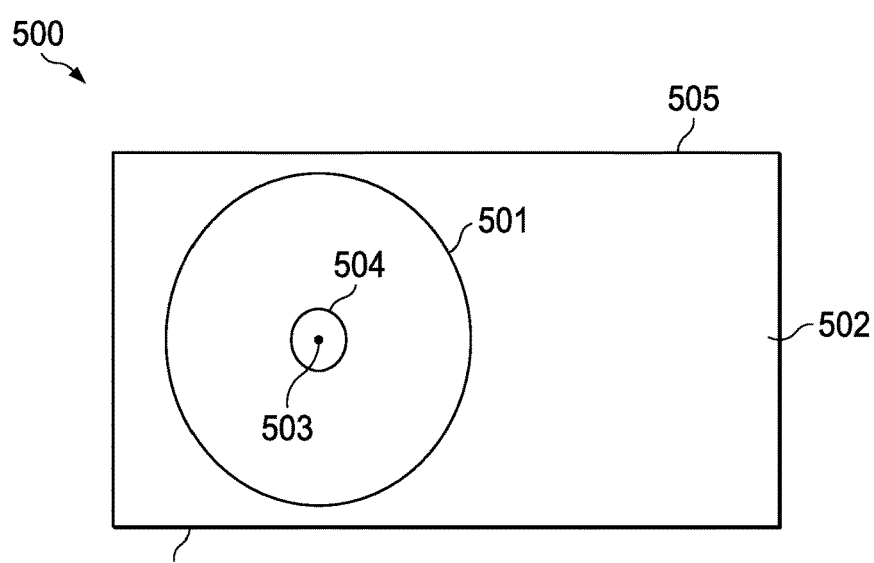
FIG. 5 shows a schematic of an exemplary detected circle positioned at the center of the vertical extent of an exemplary display.

In some implementations, the view of the magnified image presented on the display can be a portion or a subset of the field of view of the microscope and of the real-time video image. As shown in FIG. 4C, a dashed box 414 may indicate the view presented on the screen, wherein the position of the dashed lines may correspond to the edges of the display screen. Accordingly, one of the objectives of the present invention is to maximize the size of the magnified image of the detected circular shape on the display screen. In this way, a maximal area of the display screen may be utilized for displaying the magnified image of the eye to the surgeon. In some implementations, the zoom of the magnification can be set by a user, such as the surgeon to maximize the size of the magnified image of the detected circular shape on the display screen. In other implementations, the processor, executing instructions contained in the non-transitory computer-readable medium, may detect a diameter of a detected circular image, and control the zoom level of the field of view so that the diameter of the detected circular image is fitted within the edges of the display screen. In some implementations, the zoom level may be adjusted by the processor, executing instructions contained in the non-transitory computer-readable medium to send an instruction to the microscope to change the optical zoom of the microscope accordingly. In other implementations, the zoom level may be adjusted by the processor, executing instructions contained in the non-transitory computer-readable medium, to change the digital zoom of the image that is transmitted to the display accordingly. In particular, when the display is rectangular, such as a landscape-oriented screen, e.g. 16×9 aspect ratio OLED screen typically used in conjunction with the NGENUITY® system, the zoom level may be set so that the diameter of the detected circular shape is fitted within the vertical extent of the display screen. Accordingly, in some implementations, on a rectangular screen, the circular image may be positioned in the center of the display, or to one side leaving room on the rectangular display such as the exemplary 16×9 display for additional information, such as pre-operative images and/or electronic medical records. FIG. 5 shows a schematic 500 of an exemplary circle 501 positioned with its center at the center of the vertical extent of an exemplary display 502. The term "centering" as used herein may refer to positioning of the center of a circle on a display, wherein the positioning is effective to orient the center of the circle at a location at or near the middle of the screen space of a display or within a user-defined or pre-set region thereof. In some implementations, the term "centering" may refer to the positioning of the center of the circle within a set distance of the center of the display, such as within 10% of the center 503 of the display, as indicated by region 504 shown in FIG. 5. In some implementations, a display may be square, while in other implementations, the display may be rectangular. Other display shapes are also possible. With regard to a square display, the term "center of the display" may refer to a location that is approximately equidistant from each of the sides. With regard to a rectangular display, the term "center of the display" may refer to a location that is approximately equidistant from each of the sides, or in particular equidistant from each of the long sides 505 of the rectangle, as indicated by location 502 in the exemplary schematic rectangle display shown in FIG. 5. In some implementations, the centering may be performed to preferably result in the positioning of the circle so that the entire circle is visible on the display. In other implementations, the centering may be performed to result in the positioning of the circle so that only a portion of the circle is visible on the display.

In various implementations described herein, detection of the circular image may use any suitable algorithm identifiable by persons skilled in the art for detection of circles in images. Standard algorithms that may be used to detect circles include circle Hough Transform and random sample consensus (RANSAC), among others identifiably by skilled persons.

The term "Hough transform" as used herein refers to a feature extraction technique used in image analysis, computer vision, and digital image processing. The purpose of the technique is to find imperfect instances of objects within a certain class of shapes by a process termed a voting procedure. This voting procedure is carried out in a parameter space, from which object candidates are obtained as local maxima in a so-called accumulator space that is explicitly constructed by the algorithm for computing the Hough transform.

The term "circle Hough Transform" or "CHT" as used herein refers to a specialization of Hough Transform, and is a basic technique routinely used in Digital Image Processing, for detecting circular objects in a digital image. The circle Hough Transform (CHT) is a feature extraction technique for detecting circles. The purpose of the technique is to find circles in imperfect image inputs. The circle candidates are produced by "voting" in the Hough parameter space and then select the local maxima in a so-called accumulator matrix.

As persons skilled in the art would understand, in a two-dimensional space, a circle can be described by:

$$(x-a)^2+(y-b)^2=r^2 \tag{Eq. 1}$$

where (a,b) is the center of the circle, and r is the radius. If a 2D point (x,y) is fixed, then the parameters can be found according to Eq. 1. The parameter space would be three dimensional, (a, b, r). And all the parameters that satisfy (x, y) would lie on the surface of an inverted right-angled cone whose apex is at (x, y, 0). In the 3D space, the circle parameters can be identified by the intersection of many conic surfaces that are defined by points on the 2D circle.

This process can be divided into two stages. The first stage is fixing radius then find the optimal center of circles in a 2D parameter space. The second stage is to find the optimal radius in a one dimensional parameter space.

In some implementations, the radius of the circle may be fixed. If the radius is fixed, then the parameter space would be reduced to 2D (the position of the circle center). For each point (x, y) on the original circle, it can define a circle centered at (x, y) with radius R according to Eq. 1. The intersection point of all such circles in the parameter space would be corresponding to the center point of the original circle.

Figure 6:
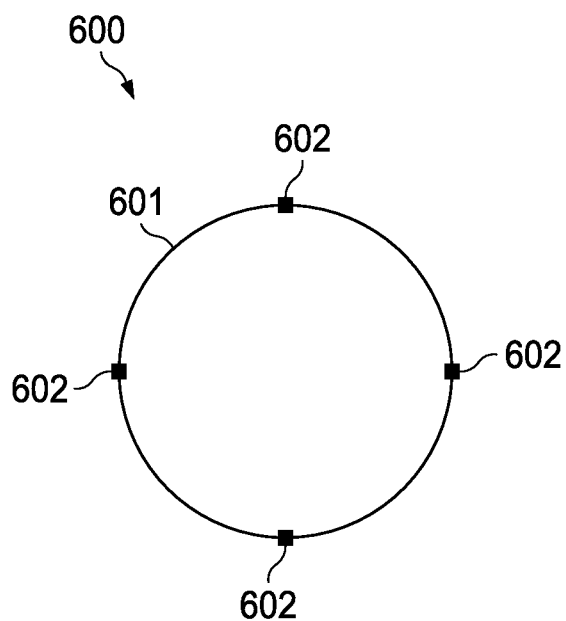
FIG. 6 shows a schematic illustrating an exemplary circular shape in an image.
Figure 7:
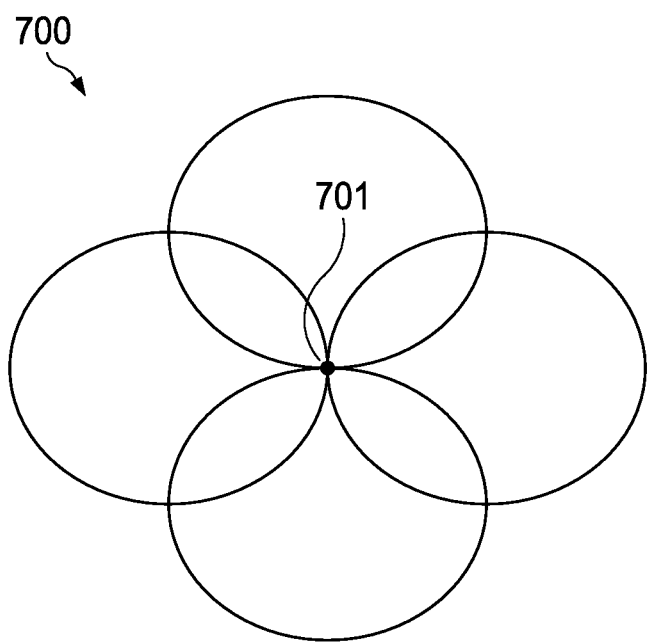
FIG. 7 shows a schematic illustrating an exemplary image related to a circle Hough transform.

For example, 4 points 602 on a circle 601 in an exemplary circle image 600 may be considered as shown in FIG. 6. An exemplary circle Hough transform 700 is shown in FIG. 7. For each (x,y) of the four points 602 in the original image 600, the circle Hough transform can define a circle in the Hough parameter space centered at (x, y) with radius r. An accumulator matrix is used for tracking the intersection point. In the parameter space, the voting number of points through which the circle passing would be increased by one. Then the local maxima point 701 (the point in the center) can be found. The position (a, b) of the maxima 701 would be the center of the original circle 601.

As would be understood by skilled persons, in practice, an accumulator matrix is introduced to find the intersection point in the parameter space. First, the parameter space is divided into "buckets" using a grid to produce an accumulator matrix according to the grid. The element in the accumulator matrix denotes the number of "circles" in the parameter space that passing through the corresponding grid cell in the parameter space. The number is also called "voting number". Initially, every element in the matrix is zeros. Then for each "edge" point in the original space, a circle can be formulated in the parameter space and increases the voting number of the grid cell which the circle passing through. This process is called "voting".

After voting, the local maxima can be found in the accumulator matrix. The positions of the local maxima correspond to the circle center in the original space.

For circles with unknown radius, since the parameter space is 3D, the accumulator matrix would also be 3D. Possible radii may be iterated through; for each radius, the previous technique is used. Finally, the local maxima is found in the 3D accumulator matrix. The accumulator array should be A[x,y,r] in the 3D space. Voting should be for each pixels, radius and theta A[x,y,r]+=1.

As would be understood by skilled persons, an exemplary algorithm is as follows: (1) For each A[a,b,r]=0; (2) Process the filtering algorithm on image Gaussian Blurring, convert the image to grayscale (grayScaling), make Canny operator, The Canny operator gives the edges on image. (3) Vote the all possible circles in accumulator. (4) The local maximum voted circles of Accumulator A gives the circle Hough space. (5) The maximum voted circle of Accumulator gives the circle.

As would be understood by skilled persons, an exemplary code for the circle Hough transform voting process is as follows:

```
For each pixel(x,y)
    For each radius r = 1Ø to r = 6Ø // the possible radius
        For each theta t = Ø to 36Ø // the possible theta Ø to 36Ø
            a = x - r = cos(t * PI / 180); // polar coordinate for center
            b = y - r = sin(t * PI / 180); //polar coordinate for center
            A[a,b,r] +=1; //voting
```

-continued

```
        end
    end
end
```

Other exemplary implementation codes are identifiable by persons skilled in the art, such as those used in MATLAB and Python.

In some implementations, the Hough Circle Detection program may be used to detect circles in images, which uses the Hough algorithm CvHoughCircles from the OpenCV library, identifiable by skilled persons. In the Hough Circle Detection program, parameters can be defined, such as minimum radius, maximum radius, and various applicable thresholds and filters identifiable by skilled persons.

In some implementations, detection of circles in images as performed by OpenCV may use the Hough Gradient method, such as the function in OpenCV referred to as "cv2.HoughCircles( )", identifiable by persons skilled in the art.

Advantages of the method and system described herein include rapid, precise automatic centering of the high magnification video image on the display, allowing continuous use of high magnification while eliminating the need for manual control of centering the video image by the surgeon, e.g. via a foot pedal joystick control, which can lead to off the screen display or inadvertent hand motion caused by foot pedal joystick activation.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A system configured for automatically centering in an XY plane a field of view of a patient's eye under high magnification during ophthalmic surgery, the system comprising:
   a processor; and
   a non-transitory computer-readable medium accessible to the processor containing instructions executable by the processor for:
      acquiring, from a photosensor, a real-time video signal representing a field of view comprising the patient's eye under high magnification by a microscope, wherein the field of view comprises an en-face XY plane, and wherein the high magnification has a value of a zoom;
      displaying on a display at least one view within the field of view corresponding to the real-time video signal, wherein the display has an area;

detecting a circular image and a diameter of the circular image in the real-time video signal, wherein the circular image comprises a target image in the field of view;

determining the location of the center of the circular image within the XY plane of the field of view;

determining the location of the center of the field of view in the XY plane;

comparing the location of the center of the circular image and the location of the center of the field of view;

upon determining a difference in the locations of the center of the circular image and the center of the field of view;

transmitting a movement instruction to a motorized microscope head configured to move the location of the microscope field of view in the XY plane, wherein the movement instruction directs movement of the microscope field of view to place the center of the field of view at the location of the center of the circular image; and transmitting a zoom instruction to adjust the zoom of the magnification so that the diameter of the detected circular image is substantially fitted within a maximal portion of the area of display;

thereby automatically moving the center of the field of view to the center of the circular image detected in the real-time video signal acquired from the field of view of the patient's eye under high magnification during ophthalmic surgery.

2. The system of claim 1 wherein the center of the field of view corresponds to a set location on the display.

3. The system of claim 2 wherein the set location on the display is the center of the display.

4. The system of claim 2 wherein the display is a rectangular display and the set location on the display is a location at a mid-point between the long sides of the rectangular display.

5. The system of claim 1 wherein the circular image corresponds to an illuminated portion of the inside of the patient's eye viewable through a pupil of the eye.

6. The system of claim 1, wherein the movement instructions transmitted to the motorized microscope head support comprise a parameter of velocity, wherein the value of the velocity is variable as a function of distance between the location of the center of the field of view and the center of the circular image.

7. The system of claim 6, wherein the value of the velocity of the movement instructions increases with increasing distance between the location of the center of the field of view and the center of the circular image.

8. The system of claim 7, wherein the value of the velocity of the movement instructions increases linearly.

9. The system of claim 7, wherein the value of the velocity of the movement instructions increases non-linearly.

10. The system of claim 1, wherein the transmitting of the instruction to adjust the value of the zoom is selected from (a) transmitting an instruction to the microscope to adjust an optical zoom of the field of view of the microscope; and (b) transmitting an instruction to the display to adjust a digital zoom of the field of view of the real-time video signal.

11. The system of claim 1, wherein the instructions contained in the non-transitory computer readable medium executed by the processor for the detecting of the circular image comprises a circle Hough transform algorithm.

12. The system of claim 1 wherein the ophthalmic surgery comprises a vitreoretinal surgery.

13. The system of claim 1 wherein the real-time video signal is a 3D video signal.

14. A method of automatically centering in an XY plane a field of view of a patient's eye under high magnification during ophthalmic surgery, comprising the steps of:

acquiring, by a processor executing instructions contained in a non-transitory computer-readable medium, from a photosensor, a real-time video signal representing a field of view comprising the patient's eye under high magnification by a microscope, wherein the field of view comprises an en-face XY plane, and wherein the high magnification has a value of a zoom;

displaying on a display, via the processor executing instructions contained in the non-transitory computer-readable medium, at least one view within the field of view corresponding to the real-time video signal, wherein the display has an area;

detecting a circular image and a diameter of the circular image in the real-time video signal, by the processor executing instructions contained in the non-transitory computer-readable medium, wherein the circular image comprises a target image in the field of view;

determining, by the processor executing instructions contained in the non-transitory computer-readable medium, the location of the center of the circular image within the XY plane of the field of view;

determining, by the processor executing instructions contained in the non-transitory computer-readable medium, the location of the center of the field of view in the XY plane;

comparing, by the processor executing instructions contained in the non-transitory computer-readable medium, the location of the center of the circular image and the location of the center of the field of view; and upon determining a difference in the locations of the center of the circular image and the center of the field of view:

transmitting, by the processor executing instructions contained in the non-transitory computer-readable memory, a movement instruction to a motorized microscope head configured to move the location of the microscope field of view in the XY plane, wherein the movement instruction directs movement of the microscope field of view to place the center of the field of view at the location of the center of the circular image; and transmitting, by the processor executing instructions contained in the non-transitory computer-readable memory, a zoom instruction to adjust the zoom of the magnification so that the diameter of the detected circular image is substantially fitted within a maximal portion of the area of display;

thereby automatically moving the center of the field of view to the center of the circular image detected in the real-time video signal acquired from the field of view of the patient's eye under high magnification during ophthalmic surgery.

* * * * *